United States Patent [19]

Halloran

[11] Patent Number: 5,089,253
[45] Date of Patent: Feb. 18, 1992

[54] HAIR CARE COMPOSITIONS CONTAINING LOW STRENGTH ELASTOMERS

[75] Inventor: Daniel J. Halloran, Midland, Mich.

[73] Assignee: Dow Corning Corporation, Midland, Mich.

[21] Appl. No.: 569,785

[22] Filed: Aug. 20, 1990

[51] Int. Cl.$^5$ .................................................. A61K 7/09
[52] U.S. Cl. ........................................ 424/47; 424/71; 424/DIG. 1; 424/DIG. 2
[58] Field of Search .............. 424/47, 70, 71, 78, 424/DIG. 1, DIG. 2; 252/DIG. 13, 174.5

[56] References Cited

U.S. PATENT DOCUMENTS

| | | | |
|---|---|---|---|
| 4,221,688 | 9/1980 | Johnson et al. | 524/251 |
| 4,344,763 | 8/1982 | Tolgyesi et al. | 424/70 X |
| 4,487,883 | 12/1984 | Homan | 524/792 |
| 4,500,339 | 2/1985 | Young et al. | 424/78 X |
| 4,501,619 | 2/1985 | Gee | 106/287.12 |
| 4,620,887 | 11/1986 | Gee | 106/287.15 |
| 4,764,363 | 8/1988 | Bolich, Jr. | 424/DIG. 1 X |
| 4,844,888 | 7/1989 | Zawadzki | 424/71 X |
| 4,902,499 | 2/1990 | Bolich et al. | 424/70 |
| 4,915,938 | 4/1990 | Zawadzki | 424/70 |

*Primary Examiner*—Thurman K. Page
*Assistant Examiner*—Susan S. Rucker
*Attorney, Agent, or Firm*—John D. Thallemer

[57] ABSTRACT

A hair treating composition for imparting curl retention to hair in which at least one film forming ingredient is applied to the hair in the form of an unfilled moisture cured low strength silicone elastomer. Upon contact with moisture the compositions cure to provide improved style retention, body and shine.

18 Claims, No Drawings

HAIR CARE COMPOSITIONS CONTAINING LOW STRENGTH ELASTOMERS

BACKGROUND OF THE INVENTION

This invention relates to new hair fixative compositions and to improved methods of providing curl retention to hair in which there is employed as the film forming ingredient certain organosilicon materials which are low strength elastomers. The term "low strength elastomers" for the purposes of this invention is understood to mean that the organosilicon material is essentially an unfilled low modulus silicone network polymer.

Fixatives are designed to provide a temporary setting effect or curl to the hair, and while the most common fixative is a hair spray which is designed to be applied to the hair after the hair has been blow dried, several specialty type fixatives can be applied either after the hair is towel dried or to dry hair, in order to provide more body and volume to the hair, and to aid in styling, modeling, and sculpting of the hair into unique new looks. This is followed by application of a hair spray in the form of an aerosol or pump spray to maintain the shape and style of the hair and provide gloss and sheen to the hair, in addition to a well groomed and natural appearance. Such special type fixatives are marketed under various names including styling gels, styling cremes, styling mousses, styling foams, styling sprays, styling spritz, styling mists, styling glazes, styling fixes; sculpting lotions, sculpting gels, sculpting glazes, sculpting sprays; glossing gels, glossing spritz; shaping gels; forming mousses; modeling spritz; finishing spritz; fixing gels; and setting lotions.

Wheather the fixative is the more common hair spray or a specialty type fixative, it will typically include a film forming additive as the hair holding agent. The film forming additive should provide hair holding properties and curl retention, little flaking or powder on combing, rapid curing or drying on hair, nonstickiness, and be easily removable by shampooing. Film forming additives are typically delivered by a solvent which is usually alcohol such as ethanol or a mixture of an alcohol and water. In the case of aerosol formulations such as hairsprays and mousses, a propellant such as isobutane, butane, propane, or dimethyl ether is an added part of the delivery system.

Examples of currently used film forming agents are shellac, polyvinylpyrrolidone-ethyl methacrylate-methacrylic acid terpolymer, vinyl acetate-crotonic acid copolymer, vinyl acetate-crotonic acid-vinyl neodeconate terpolymer, poly(vinylpyrrolidone-ethylmethacrylate) methacrylic acid copolymer, vinyl methyl ether-maleic anhydride copolymer, octylacrylamide-acrylate-butylaminoethyl-methacrylate copolymer, and poly(vinylpyrrolidone-dimethylaminoethylmethacrylate) copolymer and derivatives. These particular polymers are most suitable for alcohol based formulations such as hair sprays and pumps, and are sometimes used in water-based fixative products.

Typical organic fixative systems include what are known in the trade as GANTREZ® resins which are polymers consisting of the partial ethyl ether of the polycarboxylic resin formed from vinyl methyl ester and maleic anhydride. One of the more popular GANTREZ® resins is GANTREZ® ES 225, a product of the GAF Corporation, Wayne N. J. GANTREZ® is also a trademark of the GAF Corporation. This resin has been the film forming ingredient in such products as WHITE RAIN® and FINAL NET®. Such resins are typically employed as an ethanol based pump spray.

Organic fixative systems inherently result in such undesirable properties as loss of curl-retention with time, hygroscopicity, tackiness and dullness of apperance. In addition, organic fixative system typically have poor high temperature properties which limit their use in curling iron applications.

In accordance with the present invention, a new fixative formulation is provided which includes an unfilled low strength silicone elastomer formed via moisture cure. Advantages of using silicone elastomers over organic resins are good curl retention with time due to improved humidity resistance and lack of hygroscopicity of the silicone. In addition, the silicone elastomer leaves no residue on hair, is soluble in silicones and other resin plasticizers, provides a shine effect on hair and exhibits favorable high temperature properties which makes curling iron and hair dryer applications possible in addition to room temperature applications.

U.S. Pat. No. 4,902,499, issued Feb. 20, 1990, relates to the use of rigid silicone polymers in hair care compositions, however, the '499 patent does not teach the particular silicone elastomers of the present invention. The present invention is not concerned with rigid silicone polymers. Instead, the present invention is concerned with unfilled minimally crosslinked siloxanes which are crosslinked "in situ" using moisture cure to form a low modulus solubilized silicone network polymer with elastomeric properties. In situ crosslinking implies that while some crosslinking may occur prior to application of the composition to a substrate, the majority of crosslinking takes place when the composition is exposed to the atmosphere and applied to hair. The silicone polymers in the '499 patent, however, are filler reinforced highly crosslinked siloxanes which are previously crosslinked by methods other than moisture cure. The filler reinforced system of the '499 patent suffer from the disadvantages of poor aesthetics on hair due to the presence of large amounts of solid fillers, material opacity, a sticky and tacky feel, and poor shampoo removability. Precursors of the silicone polymers of the present invention are low molecular weight siloxanes, and these precursors provide handling improvements due to their lower viscosities, as opposed to the high molecular weight siloxanes called for in the '499 patent.

The '499 patent is directed to compositions which include conditioning polymers such as linear dialkylsiloxanes. Conditioning polymers adversely affect holding properties in fixative formulations. Therefore, the linear dialkylsiloxane polymers are eliminated or reduced in the present invention via crosslinking due to moisture cure. The method of curing and crosslinking employed by the present invention eliminates linear polymers associated with poor hair holding properties and generates a network of cross-linked polymers in the form of a solubilized low strength elastomer.

It is not known in the prior art that low strength elastomers, and/or moisture cured elastomers, employed in the amounts described, would provide the overall style retention benefits which are observed herein.

SUMMARY OF THE INVENTION

This invention is directed to a hair treating method for imparting curl retention to hair in which at least one film forming ingredient is applied to the hair. The improvement utilizes as the film forming ingredient an organosilicon compound. The organosilicon compound is an unfilled moisture cured low strength elastomer.

The invention is also directed to a hair treating composition for imparting curl retention to hair by forming a film on the hair. The film is formed by applying to the hair a composition which is a mixture of:

(A) a silanol-end-blocked polydiorganosiloxane fluid represented by the formula

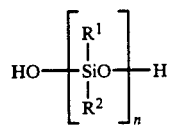

wherein $R^1$ and $R^2$ are independently selected from the group consisting of hydrogen, alkyl, alkenyl, aryl, alkylaryl, aralkyl and organo-modified alkyl and aryl groups having 1 to 22 carbon atoms; n is an integer from 5 to 15,000;

(B) an organosilicon crosslinking agent; and (C) a low molecular weight carrier.

The present invention relates to condensation cure involving moisture termed "moisture cure" or "room temperature vulcanization" (RTV). Fillers increase the strength and modulus of elastomers and one filler for a silicone elastomer is silica. Unfilled elastomers, however, are generally much weaker materials with lower moduli termed "low strength elastomers" or "zero strength elastomers". The compositions of the present invention are of the latter category and are dispersed in typical hair care delivery systems to provide homogeneous clear cohesive films and shine to the hair The invention utilized moisture or RTV cure in hair care applications to provide a thin flexible elastic silicone protective coating to the hair which protects the hair from sunlight and the elements while retaining oxygen permeability and providing good elastomeric film properties, set retention, body, bounce, humidity resistance and shine to the hair. The coating may be left on the hair for a long term effect. Longevity of the elastic silicone coating allows retention of the benefits although the treatment may be removed by conventional shampooing for a temporary effect.

These and other features, objects, and advantages, of the present invention will become more apparent when considered in light of the following detailed description thereof.

DETAILED DESCRIPTION OF THE INVENTION

The present invention relates to hair fixatives which utilize as the film forming ingredient an unfilled, moisture cured low strength elastomer. The various components of the hair fixative compositions are described below.

POLYDIORGANOSILOXANE FLUID

The compositions of the present invention contain a silanol end-blocked polydiorganosiloxane fluid having a viscosity of from about 1 to about 10,000,000 centipoise measured at 25° C. The silanol end-blocked polydiorganosiloxanes useful in the hair fixative compositions of the present invention are represented by the following:

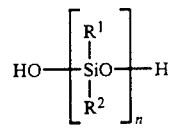

wherein $R^1$ and $R^2$ are independently selected from hydrogen, alkyl, alkenyl, aryl, and alkylaryl groups having 1 to 22 carbon atoms and organo-modified alkyl and aryl groups such as amino, epoxy, carboxy, or mercapto groups; and n is an integer from about 5 to about 15,000.

These silanol end-blocked polydiorganosiloxanes are well known in the art. Polydiorganosiloxanes useful in this invention include copolymers of various diorganosiloxane units, such as silanol end-blocked copolymers of dimethylsiloxane units or copolymers of dimethylsiloxane units, methylphenylsiloxane units, trifluoropropyl methylsiloxane units, amine-modified alkylmethylsiloxane units and methylvinylsiloxane units. Preferably, at least 50% of the $R^1$ and $R^2$ groups of the silanol end-blocked polydiorganosiloxanes are methyl groups.

The silanol end-blocked polydiorganosiloxanes employed in the practice of the present invention may vary from low viscosity fluids to viscous gums, depending upon the value of n and the nature of the particular alkyl groups represented by $R^1$ and $R^2$.

Examples of silanol end-blocked polydiorganosiloxanes useful in the hair conditioning compositions of this invention include the following:

$HOMe_2SiO(Me_2SiO)_5SiMe_2OH$ $HOMe_2SiO(Me_2SiO)_{15}SiMe_2OH$ $HOMe_2SiO(Me_2SiO)_{35}SiMe_2OH$ $HOMe_2SiO(Me_2SiO)_{283}SiMe_2OH$ $HOMe_2SiO(Me_2SiO)_{539}SiMe_2OH$ $HOMe_2SiO(Me_2SiO)_{3400}SiMe_2OH.$

The polysiloxanes comprise from about 0.01% to about 99% of the composition, preferably from about 1% to about 30%.

CROSSLINKING AGENT

Included in the hair fixative compositions of the present invention is an organosilicon crosslinking agent. Suitable crosslinking agents include silanes such as:

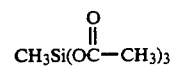

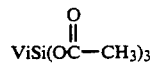

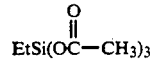

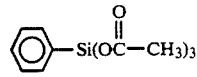

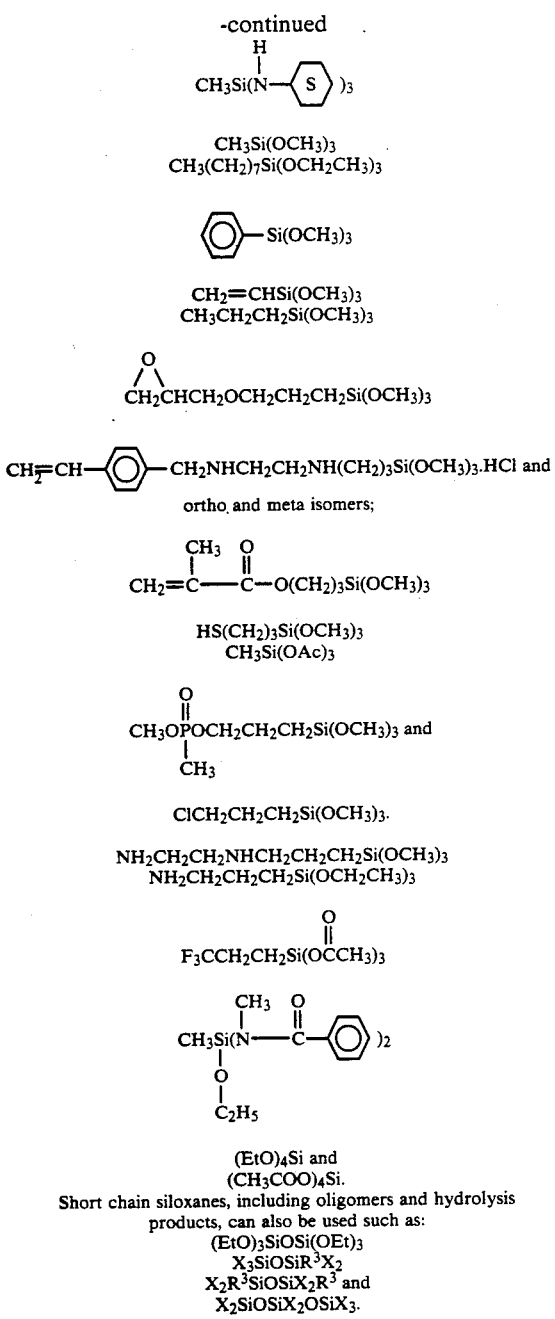

In the above formulas R³ is an alkyl group and X is a functional group such as alkoxy, acetoxy, phenoxy, cyclohexylamino, alkylamido, arylamido, alkylamino, and arylamino. Representative organosilicon crosslinking agents which may be employed are vinylmethyldiacetoxysilane, ethyltriacetoxysilane, methyltriacetoxysilane, vinyltriacetoxysilane, silicon tetraacetate, methyltriethoxysilane, methyltrimethoxysilane, dimethyltetramethoxydisiloxane, tetraethoxysilane, tetramethoxysilane, tetrapropoxysilane, bis(n-methylbenzylamido)ethoxymethylsilane, tris(cyclohexylamino)methylsilane, vinyl tris(isopropenoxy)silane, vinyltris(methylethylketoximine)silane, and methyltris(methylethylketoxime)silane. The most preferred crosslinking agents are methyltrimethoxysilane and a blend of methyltriacetoxysilane and ethyltriacetoxysilane. The crosslinking agent is present in an amount of from about 0.1% to about 20% based on the total weight of the composition.

LOW MOLECULAR WEIGHT CARRIER

The compositions of this invention include a low molecular weight carrier, or mixtures thereof, which preferably is present from about 0.1 to about 99 weight percent. Volatile low molecular weight carriers are preferred. The term "volatile" as used herein means that the material has a measurable vapor pressure. Low molecular weight carriers useful in the present invention include cyclic and linear polydimethylsiloxanes, volatile hydrocarbons, and short chain alcohols. The cyclic siloxanes have an average of about three to about seven [O—Si(CH₃)₂] repeating units per molecule and boil at atmospheric pressure from about 100° C. to about 260° C. Viscosities are generally less than 10 centipoise at 25° C. Perferably the cyclic siloxanes have an average of about 4 to about 5 repeating units per molecule. Typical examples of cyclic siloxanes are octamethylcyclotetrasiloxane and decamethylcyclopentasiloxane. The particularly preferred low molecular weight siloxanes have boiling points at ambient pressures in the range of about 99° C. to about 220° C., and viscosities at 25° C. of from about 0.65 to about 6 centistokes.

The siloxanes are the most preferred low molecular weight carriers because these volatile silicones feature high compatibility with many cosmetic ingredients and feature good solubility in most anhydrous alcohols and in many cosmetic solvents. In addition, the siloxanes are clear, essentially odorless, essentially nontoxic, nongreasy, nonstinging and evaporate without leaving a residue.

Linear polydimethylsiloxanes useful in the invention generally have viscosities of less than about 500 centipoise at 25° C. The linear volatile silicones contain from about 2 to about 9 atoms and have the formula $(CH_3)_3Si-O-[Si(CH_3)_2O]_nSi(CH_3)_3$ wherein n=0–7. Hexamethyldisiloxane is the most preferred linear polydimethylsiloxane. Also useful in compositions of the invention are certain volatile hydrocarbons. These hydrocarbons may be either straight chain or branched, and contain from about 10 to about 16 carbon atoms, preferably from about 12 to about 16 carbon atoms. Short chain alcohols such as ethanol are also suitable solvents for use in the present compositions.

CATALYST

The compostions of this invention may optionally include a catalyst. Catalysts useful in the invention are metal carboxylates, metal oxides, alkyl metal carboxylates, alkyl metal alkoxides and metal chelates. More specifically, dibutyltindiacetate, dibutyltindilaurate, stannous octoate, tetrabutyltitanate, dioctyltindilaurate and tetraisopropyltitanate are examples of catalysts that may be used. A preferred catalyst is tetrabutyltitanate which is available from E.I. DuPont di Nemours & Co., Inc., Wilmington, Del., under the trademark TYZOR® TBT. The catalyst is generally utilized at a concentration of 20 ppm to 10 weight percent.

ADDITIONAL INGREDIENTS

The hair care compositions herein can contain a variety of optional ingredients. The optional ingredients may be present in quantities such that when deposited and left on the hair they do not provide undesired properties to the hair or scalp.

Volatile organics solvents, alcohols and water can be used as a diluent for the hair conditioning composition. The use of a diluent aids in application to the hair especially when applying from a spray or aerosol. Other adjuvants which may be added to the compositions of this invention include plasticizers, thickeners, perfumes, colorants, electrolytes, pH control ingredients, antimicrobials, antioxidants, ultraviolet light absorbers and medicaments. When the fixative is in the form of a gel or lotion, it is sometimes preferred to employ a thickener in the compositions to facilitate the hand application of the composition to the hair. Thickeners are preferably used in suficient quantities to provide a convenient viscosity. For example, viscosities within the range of 400 to 6000 centipoise are preferred for lotions. High viscosities are preferred for gels whereas lower viscosities are preferred for sprays.

Suitable thickeners include sodium alginate, gum arabic, polyoxyethylene, guar gum, hydroxypropyl guar gum, cellulose derivatives such as methylcellulose, methylhydroxypropylcellulose, hydroxypropylcellulose, polypropylhydroxyethylcellulose, starch and starch derivatives such as hydroxyethylamylose and starch amylose, locust bean gum, electrolytes such as NaCl, saccharides such as fructose and glucose, and derivatives of saccharides such as PEG-120 methyl glucose dioleate. Preferred thickeners include the cellulose derivatives and saccharide derivatives. The glucose derivative, PEG-120 methyl glucose dioleate, is especially preferred in the present invention. Electrolytes including sodium chloride and ammonium chloride provide thickening particularly in aqueous systems and may also be employed in accordance with the present invention.

Representative plasticizers that may be employed include polypropylene glycol, glycerine, and polysiloxanes. Siloxane polymers such as polydimethylsiloxane, cyclic polydimethylsiloxane, phenylpolydimethylsiloxane, and polydimethylsiloxane with methylene and or propylene oxide side chains, are particularly preferred in accordance with the present invention.

The perfumes which can be used in the compositions are the cosmetically acceptable perfumes. Colorants are used to confer color to the composition and may generally be used. If used in an aqueous media, it may be preferred to employ an acid or base to adjust the pH within the range of 5 to 9 or more preferably within the range of 6 to 8 in the compositions of this invention. Any water soluble acid such as a carboxylic acid or a mineral acid is suitable. For example, suitable acids include mineral acids such as hydrochloric, sulfuric, and phosphoric, monocarboxylic acids such as acetic acid, lactic acid, or propionic acid; and polycarboxylic acids such as succinic acid, adipic acid and citric acid. Where a base is required, organic amines may be added such as 2-amino-2-methyl-1-propanol.

A preservative may be required if the present composition is employed in an aqueous medium. Representative preservatives which may be employed include about 0.1-0.2 weight percent of compounds such as formaldehyde, dimethyloldimethylhydantoin, 5-bromo-5-nitro-1, 3-dioxane, methyl- and propyl para-hydroxybenzonates, and mixtures of such benzoates with sodium dehydroacetate, sorbic acid, and imidazolidinyl urea.

The compositions of the present invention may also be formulated to include dyes, colorants, reducing agents, neutralizing agents, and preservatives, necessary for their application as permanent wave systems or hair dyes, for example. The active formulation can be applied in serveral different forms including lotions, gels, mousses, aerosols, and pump sprays, for example, and as conditioners and shampoos. The active ingredient includes a carrier, and suitable carrier fluids for hair care formulations are silicone as well as, for example, such fluids as alcohols namely ethanol or isopropanol, hydrocarbons and halogenated hydrocarbons such as mineral spirits and trichloroethane, supercritical fluids such as supercritical carbon dioxide and nitrogen, water, and aerosol propellants. In those instances where it is desired to incorporate the active in the form of either an emulsion or microemulsion, such emulsions may be prepared in accordance with either U.S. Pat. No. 4,501,619, issued Feb. 26, 1985, which is directed to emulsions, or U.S. Pat. No. 4,620,878, issued Nov. 4, 1986, relating to microemulsions, each of which is incorporated herein by reference.

When the composition is intended for aerosol application, propellant gases can be included such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether. Where the solvent system is alcohol free, mechanical and chemical drying agents may also be employed in spray and aerosol formulations.

The hair fixative compositions of the present invention can vary over a large range of concentrations ranging from very low three weight percent systems for shine and body treatment to high thirty weight percent systems for set retention. The compositions are prepared by simply blending or mixing the silanol end-blocked polydiorganosiloxane fluid, the crosslinking agent, and the low molecular weight carrier with any optional ingredients. The components are preferably present at room temperature during mixing. Such a mixture may be stored for an indefinite period of time, as long as moisture is excluded. Upon contact with moisture, such as that present in the air, the mixture cures to form an unfilled moisture cured low strength elastomer on the substrate.

The amount of the crosslinking agent mixed with the silanol end-blocked polydiorganosiloxane can vary within wide limits. However, for best results, it is preferred to add an excess of one mole of the crosslinking agent per mole of silanol groups in the silanol end-blocked polydiorganosiloxanes. The temperature at which the crosslinking agent and the silanol end-blocked polydiorganosiloxane are mixed is not critical and a room temperature addition is usually employed. The blending or mixing of the silanol end-blocked polydiorganosiloxane fluid, the crosslinking agent and any optional ingredients, is carried out in the presence of a low molecular weight carrier. The low molecular weight carrier reduces the overall viscosity of the composition. Other processing aids such as preservatives, adhesion promoters, flame retardants, pigments, cure accelerators, antioxidants, softners, extenders, or plasticizers may also be used.

Hair car formulations which include the fixative compositions of the present invention include shampoos, conditioners, hairsprays, styling gels, tonics, lotions and mousses, and may be in the form of nonaqueous, aqueous or aqueous-alcoholic dispersions, thickened or unthickened creams, gels, aerosol foams or sprays. The compositions provide increased style retention, bounce, body, shine and provide a protective coating to the hair.

The invention will be further illustrated by a consideration of the following examples. All parts and percentages in the examples are on a weight basis unless otherwise stated.

EXAMPLE 1

Into a flask was placed:
8.94 g. hydroxy terminated polydimethylsiloxane
100.00 g. dimethylcyclosiloxane
0.28 g. ethyltriacetoxysilane
0.28 g. methyltriacetoxysilane
0.01 g. dibutyltindiacetate.

The contents were mixed until uniform. A clear, homogenous low viscosity solution was obtained.

EXAMPLE 2

Into a flask was placed:
47.40 g. hydroxy terminated polydimethylsiloxane
150.80 g. dimethylcyclosiloxane
1.50 g. ethyltriacetoxy silane
1.50 g. methyltriacetoxysilane
0.01 g. dibutyltindiacetate.

The contents were mixed until uniform. A clear, homogenous low viscosity solution was obtained.

EXAMPLE 3

Into a flask was placed:
28.50 g. hydroxy terminated polydimethylsiloxane
171.80 g. dimethylcyclosiloxane
0.50 g. ethyltriacetoxy silane
0.50 g. methyltriacetoxysilane
0.01 g. dibutyltindiacetate.

The contents were mixed until uniform. A clear, homogenous low viscosity solution was obtained.

EXAMPLE 4

Into a flask was placed:
7.90 g. hydroxy terminated polydimethylsiloxane
91.60 g. dimethylcyclosiloxane
0.50 g. methyltrimethoxysilane
0.05 g. tetrabutyltitanate.

The contents were mixed until uniform. A clear, homogenous low viscosity solution was obtained.

EXAMPLE 5

Into a flask was placed:
7.90 g. hydroxy terminated polydimethylsiloxane
91.60 g. hexamethyldisiloxane
0.25 g. ethyltriacetoxy silane
0.25 g. methyltriacetoxysilane
0.04 g. dibutyltindiacetate.

The contents were mixed until uniform. A clear, homogenous low viscosity solution was obtained.

EXAMPLE 6

Into a flask was placed:
7.90 g. hydroxy terminated polydimethylsiloxane
91.60 g. dimethylcyclosiloxane
0.13 g. ethyltriacetoxy silane
0.13 g. methyltriacetoxysilane
0.25 g. ethylenediamine-propyltrimethoxysilane
0.01 g. dibutyltindiacetate.

The contents were mixed until uniform. A clear, homogenous low viscosity solution was obtained.

EXAMPLE 7

Hair fixative formulations were evaluated by employing six inch hair tresses of approximately two grams of untreated hair. Each tress was made by gluing the top part of the hair to a 2"×2" plastic tab. After drying on the tab, the hair was trimmed to six inches. Each tress was then cleaned with a shampoo of the following formulation:
61.45 g. distilled Water
0.05 g. methychlorisothiazolinone and methylisothiazolinone
35.00 g. ammonium Lauryl Sulfate
3.00 g. lauramide DEA
0.50 g. 0.5% Ammonium Chloride Solution
q.s. sulfuric acid.

Each tress was first rinsed for 15 minutes under 40 degree Centigrade tap water and 0.5 cc of the above shampoo was applied. Shampooing for 30 seconds was followed by a 30 second rinse. The tresses were then set on plastic rollers approximately ½ inch in diameter and allowed to dry overnight. Hair fixative formulations were applied to the hair either by dripping on 0.5 g or by spraying on 0.3 g. If the drip application was used, the hair was combed three times and reset on a roller. If the solution was delivered from a pump, the hair was not reset. The solution was allowed to cure on the hair. The dried tresses were hung in a constant humidity chamber and initial readings were taken as well as additional readings at predetermined intervals. If the tress was reset, the roller was removed prior to exposure. Curl retention was calculated as the extended length minus the length at the end of the predetermined interval divided by the extended length minus the initial length. The results shown in Tables I, II and III represent curl retention after 24, 48 and 50 hours of exposure, respectively.

EXAMPLE 8

Hair tresses were prepared, shampooed and dried in accordance with Example 7. Two grams each of the materials prepared in Examples 1-6 were dropped onto dry hair tresses. Upon contact with moisture in the hair, the fixative mixture cured to form an elastomeric film on the hair. The treated tresses were combed three times and wound onto a hot curling iron where the tresses remained for three minutes. The tresses were unrolled and hung in air at 50% relative humidity.

TABLE I

| Results of Curl-Retention Test | | | | |
|---|---|---|---|---|
| Composition | Cure (hours) | Temperature (°C.) | Relative Humidity | Curl Retention 24 hrs. |
| Example 1 | 20 | 23 | 70% | 67 |
| Example 2 | 20 | 23 | 70% | 100 |
| Example 5 | 20 | 23 | 70% | 97 |
| Control | 20 | 23 | 70% | 64 |

The control refers to a hair tress which was shampooed but not treated with any of the compositions set forth in Examples 1-6. Table I indicates that hair treated with the unfilled moisture cured low strength elastomers of the present invention exhibits higher levels of curl retention than untreated hair after 24 hours of exposure.

TABLE II
Results of Curl-Retention Test

| Composition | Cure (hours) | Temperature (°C.) | Relative Humidity | Curl Retention (48 hrs.) |
|---|---|---|---|---|
| Example 2 | 20 | 23 | 24 hrs. at 70% | 96 |
| | | | 24 hrs. at 90% | |
| Example 5 | 20 | 23 | 24 hrs. at 70% | 94 |
| | | | 24 hrs. at 90% | |
| Control | 20 | 23 | 24 hrs. at 70% | 0 |
| | | | 24 hrs. at 90% | |

Table II indicates that the hair treated with the unfilled moisture cured low strength elastomers of the present invention exhibits improved levels of curl retention than untreated hair after 48 hours of exposure. In addition, the treated hair had a more natural feel and appearance.

TABLE III
Results of Curl-Retention Test (Example 8)

| Composition | Relative Humidity | Temperature (°C.) | Curl (3 hrs.) | Retention (50 hrs.) |
|---|---|---|---|---|
| Example 1 | 50% | 23 | 86 | 72 |
| Example 2 | 50% | 23 | 100 | 93 |
| Example 3 | 50% | 23 | 100 | 96 |
| Example 4 | 50% | 23 | 78 | 69 |
| Example 5 | 50% | 23 | 100 | 95 |
| Example 6 | 50% | 23 | 76 | 76 |
| Control | 50% | 23 | 36 | 17 |

Table III indicates that hair treated with the unfilled moisture cured low strength elastomers of the present invention exhibits much higher levels of curl retention than untreated hair.

It should be noted that while it is preferred to cure the mixture at room temperature, curing may be effected by the application of heat. In either case, the mixture of components (A), (B), and (C), is applied from a container to the hair substrate to be treated. Upon exposure to the atmosphere, moisture causes the mixture to cure forming an elastic silicone film on the hair. Curing of the film may be continued at room temperature or accelerated by applying heat to the hair by means of a heated curling iron or heated rollers. Only minimum curing if any is effected in the container itself, although in aqueous systems curing in the container would exceed that in otherwise anhydrous delivery. Once the container is opened, however, all of the contents should be used in that application.

It will be apparent from the foregoing that many other variations and modifications may be made in the compounds, compositions, and methods, described herein, without departing substantially from the essential features and concepts of the present invention. Accordingly, it should be understood that the forms of the invention described herein are exemplary only and are not intended as limitations on the scope of the present invention as defined in the appended claims.

That which is claimed is:

1. In a hair treating method for imparting curl retention to hair in which at least one film forming ingredient is applied to the hair, the improvement consisting essentially of applying to the hair a mixture of:
(A) a silanol-end-blocked polydiorganosiloxane fluid represented by the formula

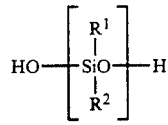

wherein $R^1$ and $R^2$ are independently selected from the group consisting of hydrogen, alkyl, alkenyl, aryl, alkylaryl, aralkyl and organo-modified alkyl and aryl groups having 1 to 22 carbon atoms; n is an integer from 5 to 15,000;
(B) an organosilicon crosslinking agent; and
(C) a low molecular weight carrier; curling the mixture by contact with moisture to form an unfilled low strength silicon elastomer and utilizing the elastomer as the film forming ingredient.

2. The method of claim 1 wherein the organo-modified group is selected from the group consisting of amino, epoxy, carboxy and mercapto.

3. The method of claim 1 wherein the silanol end blocked polydiorganosiloxane fluid has a viscosity of from about 1 to about 10,000,000 centipoise at 25° C.

4. The method of claim 1 wherein the silanol end blocked polydiorganosiloxane fluid is present in an amount from about 0.01% to about 99% of the composition.

5. The method of claim 4 wherein the silanol end blocked polydiorganosiloxane fluid is present in an amount from about 1% to about 30% of the composition.

6. The method of claim 1 wherein the crosslinking agent is selected from the group consisting of silane monomers and short chain siloxanes.

7. The method of claim 6 wherein the crosslinking agent is methyltrimethoxysilane.

8. The method of claim 6 wherein the crosslinking agent is a blend of methyltriacetoxysilane and ethyltriacetoxysilane.

9. The method of claim 6 wherein the crosslinking agent is present in an amount of from about 0.1 to about 20 weight percent.

10. The method of claim 1 wherein the low molecular weight carrier is selected from the group consisting of cyclic siloxanes, linear siloxanes, volatile hydrocarbons and short chain alcohols.

11. The method of claim 10 wherein the low molecular weight carrier is present from about 0.1 to about 99 weight percent.

12. The method of claim 1 including a catalyst.

13. The method of claim 12 wherein the catalyst is selected from the group consisting of metal carboxylates, alkyl metal carboxylates, alkyl metal alkoxides, and metal chelates.

14. The method of claim 13 wherein the catalyst is dibutyltindiacetate.

15. The method of claim 13 wherein the catalyst is tetrabutyltitanate.

16. The method of claim 1 in which the mixture includes at least one additional ingredient selected from the group consisting of propellants, plasticizers, thickeners, preservatives and fragrances.

17. The method of claim 1 wherein the mixture is cured at room temperature.

18. The method of claim 1 wherein the mixture is cured by the application of heat.

* * * * *